United States Patent [19]

Myers et al.

[11] 4,161,463
[45] Jul. 17, 1979

[54] OLEFIN DISPROPORTIONATION OVER SILICA-RARE EARTH METAL OXIDE CATALYSTS

[75] Inventors: John W. Myers; Jesse R. Harris, both of Bartlesville, Okla.

[73] Assignee: Phillips Petroleum Company, Bartlesville, Okla.

[21] Appl. No.: 908,606

[22] Filed: May 23, 1978

Related U.S. Application Data

[62] Division of Ser. No. 739,765, Nov. 8, 1976, Pat. No. 4,102,939.

[51] Int. Cl.$^2$ .......................... B01J 29/06; B01J 23/10
[52] U.S. Cl. ................................ 252/455 R; 252/462
[58] Field of Search ........................... 252/455 R, 462

[56] References Cited

U.S. PATENT DOCUMENTS

| 2,884,460 | 4/1959 | Komerewsky | 252/462 X |
| 3,009,871 | 11/1961 | Komarewsky | 252/462 X |
| 3,836,481 | 9/1974 | Kajimoto et al. | 252/462 |
| 3,899,445 | 8/1975 | Kajimoto et al. | 252/462 |

*Primary Examiner*—Carl Dees

[57] ABSTRACT

Olefins, such as n-hexene, are disproportionated under reaction conditions with a catalyst of an oxide of yttrium, lanthanum, cerium, praseodymium, or dysprosium, on a silica support.

20 Claims, No Drawings

OLEFIN DISPROPORTIONATION OVER SILICA-RARE EARTH METAL OXIDE CATALYSTS

This is a divisional application of Ser. No. 739,765, filed Nov. 8, 1976, now U.S. Pat. No. 4,102,939, patented July 25, 1978.

FIELD OF THE INVENTION

The invention pertains to the disproportionation of olefins. In another aspect, the invention pertains to a catalyst system of an oxide of yttrium, lanthanum, cerium, praseodymium, or dysprosium on a silica support.

BACKGROUND OF THE INVENTION

Processes and catalysts for converting olefinically unsaturated compounds into other olefinically unsaturated compounds have been studied for some years. The reaction involved has come to be termed the "olefin reaction." Catalysts having activity for such reactions have been studied at length for the purpose of improving the performance generally, or in specific situations. Still, the search continues for catalysts and processes effective for the olefin reaction.

SUMMARY OF THE INVENTION

We have discovered that monoolefinic hydrocarbons can be converted in accordance with the olefin reaction by catalysts comprising certain rare earths in oxide form on a silica support. These rare earth oxides are the oxides of yttrium, lanthanum, cerium, praseodymium, and dysprosium. Most unexpectedly, we have found that these silica-supported catalysts are quite efficient, but that the corresponding alumina-supported materials are not effective. We also have found among the rare earths that neodymium is not effective.

DETAILED DESCRIPTION OF THE INVENTION

The catalysts according to one aspect of our invention are selected from one or more rare earth metal oxides selected from the yttrium subgroup and the cerium subgroup, as these groups are designated by Latimer and Hildebrand, Reference Book of Inorganic Chemistry, Revised Ed. (The Macmillan Company 1940), on a silica support. And of the groups, however, neodymium-containing catalysts are not effective in the process of this invention. These catalysts are particularly useful in our process of olefin disproportionation.

More particularly, the rare earths suitable in preparing our catalysts in accordance with one aspect of our invention are selected from yttrium, lanthanum, cerium, praseodymium, and dysprosium, any of these alone, or in mixture, as the metal oxide, supported on silica. Unexpectedly, the same rare earth metal oxides but on a support of alumina are not effective.

Preferably and conveniently, since it takes less of the rare earth metal and still results in high effectiveness, the metal oxides are employed on a support of silica. The amount of rare earth metal contained in the finished catalyst, calculated as the metal, can vary widely, though on an exemplary and practical basis from about 0.05 to 20 weight percent, based on the total weight of catalyst, that is of the rare earth metal oxide plus silica employed, more preferably about 0.5 to 15 weight percent.

The catalysts can be prepared in any convenient fashion, such as by dry mixing of the oxide and particulate silica, impregnation of silica with a solution containing 1 or more rare earth metal compounds, and the like, as known in the catalyst preparation arts. The silica employed should be of a good catalytic grade, and it is preferred that the specific surface area be reasonably high, though this did not appear to be critical but is a preference for maximum activity. Presently preferred is a silica with a specific surface area ranging from such as about 10 to 100 square meters per gram, more preferably from about 50–100 square meters per gram.

While the silica supported catalyst can be prepared in any convenient fashion, one effective method is to impregnate the silica with a solution containing one or more rare earth metal salts which are convertible to the oxide on calcination in a molecular oxygen atmosphere. Typical and suitable of such rare earth metal salts are the bromates, halides, nitrates, sulfates, various organic complexes such as those derived from ethylene diamine tetra-acetic acid, and the like, presently preferred being the nitrates for ease and convenience of dissolving and handling. After impregnation of the support, the composite is dried, and calcined in a molecular oxygen-containing atmosphere, such as air, at a suitable calcining temperature, such as about 600° F. to 1500° F. (about 315° to 816° C.), presently suitably and preferably from about 800° F. to 1200° F. (about 426° to 649° C.), for a time suitable to effectuate the conversion of the rare earth metal salt to the oxide, typically for such as about 1 to 20 hours.

After calcining, the catalysts can be activated at elevated temperatures in gases such as air, hydrogen and nitrogen and mixtures thereof. The choice of gas appears to be related to the catalyst. Praseodymium-containing catalysts are preferably activated in air, whereas cerium-containing supported catalysts are preferably activated in hydrogen, for example.

The finished catalyst then can be formed in any conventional manner to provide suitable size particles, powders, pills, wafers, agglomerates, extrudates, or the like, depending on the particular reactor configuration and design.

Prior to using the catalysts in a disproportionation process, it presently is preferred in most instances to activate the catalysts by heating at elevated temperatures. The temperatures preferably are somewhat above the temperatures expected to be employed in the process, for example such as about 100° to 400° F. above the expected process temperatures, more usually about 150° to 250° F. above. The elevated temperature activation step is conducted with the catalyst in a nitrogen, hydrogen, or mixture atmosphere, and can be coupled with an initial pre-treatment at activation temperature in a molecular oxygen-containing gas, if desired. The time of activation can vary widely, from such as less than about 1 hour to 24 hours or more. The praseodymium catalysts preferably omit this step, though with some feedstocks it may be found desirable.

FEEDSTOCKS

The term olefin reaction describes a reaction of which the primary reaction can be visualized as a reaction comprising the breaking of two existing unsaturated bonds between first and second carbon atoms and between third and fourth carbon atoms, respectively, and the formation of two new unsaturated bonds between said first and third and between said second and fourth carbon atoms. Said first and second carbon atoms and said third and fourth carbon atoms can be in the same or different molecules.

In the present application the term "olefin reaction" designates the reaction of monoolefinically unsaturated compounds. The term disproportionation is used to define one aspect of this reaction. Monoolefins suitable for conversion according to the process of our invention include the following:

1. Acyclic monoolefins, including those of aryl, cycloalkyl and cycloalkenyl substituents, containing 3 to 20 carbon atoms per molecule with no branching closer than the 3-position to the double bond, containing no quaternary carbon atoms, and containing no aromatic substituents closer than the 4-position to the double bond. Representative compounds include propylene, 1-butene, 2-butene, 1-pentene, 2-pentene, 3-methylbutene-1, 1-hexene, 2-hexene, 4-octene, 2-nonene, 3-decene, 8-ethyldecene-2, 4-dodecene, vinylcyclohexane, 4-vinylcyclohexane, 1-eicosene, and the like, alone or in admixture.

2. A mixture of ethylene and one or more acyclic unsaturated internal monoolefins containing 3 to 20 carbon atoms per molecule, such as ethylene and 3-hexane.

3. Cyclopentene.

4. Cyclic and bicyclic monoolefins containing 7 to 12 ring carbon atoms, including those substituted with up to 3 alkyl groups containing up to about 5 carbon atoms per group, containing no branching closer than the 3-position, and containing no quaternary carbon atoms closer than the 4-position to the double bond, including mixtures of such monoolefins with cyclopentene. Representative of such compounds are cycloheptene, cyclooctene, 4-methylcyclo octene, cyclononene, 3-methyl-5-ethylcyclodecene, cyclododecene, norbornene, and the like, alone, or in admixture, or in admixture as mentioned with cyclopentene.

5. A mixture of one or more of the described monocyclic monoolefins containing 7 to 12 ring carbon atoms with either ethylene, or with one or more unsubstituted acyclic monoolefins as described. Typically, such would include ethylene and cycloheptene, propylene and cyclodecene, 2-pentene and cyclooctene, ethylene and cyclododecene, and the like.

CONVERSION CONDITIONS

The feedstocks are converted by contact with the selected catalyst under reaction conditions in a batchwise or continuous process in the vapor phase or liquid phase using any suitable mode of contact or reaction apparatus. The process can be carried out in the absence or presence of a nonreactive diluent. Suitable diluents include propane, n-pentane, n-hexane, isooctane, dodecane, cyclohexane, methylcyclohexane and mixtures thereof, including primarily those paraffins and cycloparaffins having up to about 12 carbon atoms per molecule.

The reaction temperature can vary from about 400° to about 1200° F. (204°–649° C.), more preferably from about 600° to about 900° F. (315°–482° C.). The reaction pressure can vary from about 0.1 to about 2,000 psig (0.7–13,800 kPa gage) and generally any convenient pressure in this range can be employed. In continuous processes, the feed rate will vary according to the feedstock being converted and the desired degree of conversion, but will generally be in the range from about 0.1 to about 50 volumes feed per volume catalyst per hour (LHSV) if the reaction is carried out in liquid phase, and between about 100 to about 5,000 volumes feed per volume catalyst per hour (GHSV) if the reaction is effected in the gas phase. According to our work, employment of the higher described reaction temperatures tends to require employment of the higher rates of LHSV or GHSV to maintain disproportionation and minimize cracking. In batch operations, which are less preferred, the reaction time can vary from about 0.1 to about 20 hours, with the shorter times preferred as reaction temperatures are increased, so as to maintain disproportionation and minimize cracking.

The effluent from the reaction zone can be separated into its components by any conventional means such as distillation and recovered. Unconverted materials can be recycled through the reaction zone, if desired.

Spent catalyst can be recovered and regenerated conventionally by calcining in air at elevated temperature.

EXAMPLES

Examples are provided to assist one skilled in the art to an understanding of the invention. Particular species, conditions, reaction parameters, and the like, are designed to be illustrative, and not limitative of the scope of the invention.

EXAMPLE I

A catalyst was prepared by impregnating 10 - 20 mesh (U.S. Sieve Series) catalytic grade silica having a specific surface area of about 88 $m^2/g$ with an aqueous solution of praseodymium nitrate, drying the composite, and calcining the dried material at 900° F. in air for 2 hours. The final catalyst was calculated to contain 10 percent praseodymium oxide calculated as the metal and 90 wt. percent silica.

A tubular reactor was charged with 20 cc of the catalyst, the reactor was heated to 900° F. and air was passed through it for 2 hours and then nitrogen overnight (about 15 hours). The reactor was cooled to 705° F. (374° C.) and hexene-1 was passed through it at atmospheric pressure for 0.7 hour at the rate of 0.5 LHSV. The effluent was cooled and the liquid portion collected in a wet ice trap and analyzed by gas-liquid chromatography. The results obtained are presented in Table 1.

Table 1

| Disproportionation of Hexene-1 Over a Catalyst of Praseodymium Oxide/Silica Activated in Nitrogen | | |
|---|---|---|
| Total Conversion, Mole % | 29.5 | Wt. % Based |
| Liquid Composition, Wt. % | | on Converted Hexene |
| Butenes 3.9 } | 10.8 | 35.5 |
| Pentenes 6.9 | | |
| Hexenes 69.6 | | |
| Heptenes 8.8 } | | |
| Octenes 5.6 | | |
| Nonenes 3.3 } | 19.6 | 64.5 |
| Decenes 1.2 | | |
| Undecenes 0.5 | | |
| Dodecenes 0.2 | | |

The results show the liquid product contained 10.8 wt. percent olefins lower in molecular weight than hexene and 19.6 wt. % olefins higher in molecular weight than hexene. In terms of hexene converted, olefins lower in molecular weight than hexene constituted 35.5 wt. % of the products and olefins higher in molecular weight than hexene constituted 64.5 wt. % of the products.

EXAMPLE II

A series of catalysts was prepared by impregnating catalytic grade alumina having a specific surface area of about 296 m²/g or the previously described silica having a specific surface area of about 88 m²/g with an aqueous solution of a metal nitrate selected from the yttrium metal subgroup or the cerium metal subgroup. Each composite was dried and calcined for 2 hours at 900° F. in air and cooled. Each catalyst was calculated to contain 10 wt. percent metal (in oxide form) and 90 wt. % support.

In each run a tubular reactor was charged with 20 cc of catalyst and heated to 900° F. in hydrogen and then hydrogen was passed through the reactor overnight (about 15 hours). The reactor then was cooled to about 705° F., flushed with nitrogen and hexene-1 was passed through the reactor. The liquid effluent was collected as before. The metals used, conditions employed, and results obtained are presented in Table 2.

Neodymium, however, in Run 8, proved to be ineffective.

Runs 4 and 7, directly comparable with Runs 3 and 6, respectively, show that inert catalysts for disproportionation under the conditions employed result when alumina was selected as the support instead of silica.

EXAMPLE III

A catalyst was prepared by impregnating a silica, having a surface area of 88m²/g, with an aqueous solution of cerous nitrate, drying, and then calcining the dried composite in air from the indicated time at 900° F., followed by the indicated pretreatment step. The calcined composite was calculated to contain about 10 weight percent cerium oxide calculated as Ce.

In each run, a tubular reactor was charged with 20 cc of catalyst, and pretreated (activated). After pretreatment, the reactor was cooled to about 705° F., flushed with nitrogen, and hexene-1 was passed through the reactor. The conditions used and results obtained are shown in Table 3:

Table 2

Disproportionation of Hexene-1

| Catalyst No. | 2 | 3 | 4 | 5 | 6 | 7 | 8 | 9 |
|---|---|---|---|---|---|---|---|---|
| Run No. | 2 | 3 | 4 | 5 | 6 | 7 | 8 | 9 |
| Rare Earth | Y | La | La | Ce | Pr | Pr | Nd | Dy |
| Support | silica | silica | alumina | silica | silica | alumina | silica | silica |
| Pretreatment | hydrogen 900° F., 15 hr. | hydrogen 900° F., 15 hr. | hydrogen 900° F., 15 hr. | hydrogen 900° F., 15 hr. | hydrogen 900° F., 15 hr. | hydrogen 900° F., 15 hr. | hydrogen 900° F., 15 hr. | hydrogen 900° F., 15 hr. |
| Process Conditions | | | | | | | | |
| Temp., °F. | 704 | 705 | 705 | 705 | 706 | 702 | 705 | 704 |
| Feed LHSV | 0.5 | 0.5 | 0.5 | 0.5 | 0.5 | 0.4 | 0.5 | 0.5 |
| Run Length, Hrs. | 0.3 | 0.3 | 0.3 | 0.3 | 0.4 | 0.3 | 0.3 | 0.3 |
| Liquid Product, Wt. % | | | | | | | | |
| Olefins lower in molecular weight than hexene (wt. % based on converted hexene) | 5.0 (54.9) | 4.5 (57.0) | 0 (0) | 8.7 (59.6) | 5.0 (56.8) | 0 (0) | 0.2 (100) | 4.3 (56.6) |
| Hexene | 90.9 | 92.1 | 100.0 | 85.4 | 91.2 | 99.7[1] | 99.8 | 92.4 |
| Olefins higher in molecular weight than hexene (wt. % based on converted hexene) | 4.1 (45.1) | 3.4 (43.0) | 0 (0) | 5.9 (40.4) | 3.8 (43.2) | 0 (0) | 0 (0) | 3.3 (43.4) |
| Hexene Conversion, Wt. % | 9.1 | 7.9 | 0 | 14.6 | 8.8 | 0 | 0.2 | 7.6 |

[1]0.3 wt. % methylcyclopentane found in effluent.

The results of Runs 2, 3, 5, 6 and 9 show that active catalysts for disproportionation were obtained when a rare earth selected from one of yttrium, lanthanum, cerium, praseodymium, or dysprosium was dispersed on a silica support.

Table 3

| Run No. | 10 | 11 | 12 |
|---|---|---|---|
| Calcining | air, 2 hr. 900° F. | air, 2 hr. 900° F. | air, 4.5 hr. 900° F. |
| Pretreatment | | | |
| Temp. °F. | 900 | 1100 | 900 |
| Gas | ≈16 hr. in H₂ | ≈16 hr. in H₂ | ≈15 hr. in N₂ |
| Process Conditions[a] | | | |
| Temp. °F. | 704 | 703 | 704 |
| Press. psig | 0 | 0 | 0 |
| LHSV | 0.6 | 0.6 | 0.5 |
| Length of Run, Hr. | 0.25 | 0.33 | 0.33 |
| Liquid Product Comp., Wt. % | | | |
| Olefins lower in mol. wt. than hexene | 3.1 | 1.4 | 0.9 |
| Hexene | 94.8 | 97.8 | 98.6 |
| Olefins higher in mol. wt. than hexene | 2.1 | 0.8 | 0.5 |
| Hexene Conversion, Wt. % | 5.2 | 2.2 | 1.4 |

[a]The hexene feed was purged with helium to remove dissolved oxygen and passed over MgO (previously activated at 800° F.) at room temperature to remove impurities.

The results in Table 3 demonstrate that prereducing in H₂ results in a more active catalyst than pretreating in N₂. The results also show that prereducing at 900° F. is preferable to prereducing at 1100° F.

EXAMPLE IV

Portions of catalyst prepared as described in Example III were pretreated and tested with hexene-1 feed as shown in Table 4.

Table 4

| Run No. | 5 | 13 | 14 | 15 |
|---|---|---|---|---|
| Calcining | 2 hr., 900° F., air | 2 hr., 900° F., air | 2 hr., 900° F., air | 2 hr., 900° F., air |
| Pretreatment | | | | |
| Temp., °F. | 900 | 900 | 900 | 900 |
| Gas | ≈16 hr. in $H_2$ | Regenerated in air-$N_2$ mixture for ≈65 hr., purged with $N_2$, and cooled to 700° F. in $H_2$ in ≈0.9 hr. | ≈16 hr. in $H_2$ | ≈16 hr. in $H_2$ |
| Process Conditions | | | | |
| Temp. °F. | 705 | 704 | 703 | 704 |
| Press., psig | 0 | 0 | 0 | 0 |
| LHSV | 0.5 | 0.5 | 0.5 | 0.5 |
| Length of Run, Hr. | 0.33 | 0.33 | 0.33 | 0.33 |
| Liquid Product Composition, Wt. % | | | | |
| Olefins lower in mol. wt. than hexene | 8.7 | 2.3 | 5.4 | 6.1 |
| Hexene | 85.4 | 96.6 | 90.8 | 86.5 |
| Olefins higher in mol. wt. than hexene | 5.9 | 1.1 | 3.8 | 7.4 |
| Hexene Conversion, Wt. % | 14.6 | 3.4 | 9.2 | 13.5 |

Run 5 is the same run shown as Run 5 in Table 2. The same portion of catalyst was used in Runs 5 and 13. After Run 5, intervening runs were made at 807° F. and 909° F. and the catalyst was regenerated in an air-$N_2$ mixture at about 900° F., and reduced in hydrogen while being cooled to the approximate 700° F. test temperature of Run 13. Comparison of Runs 5 and 13 shows that the catalyst was much less active after regeneration in Air-$N_2$ and reducing in $H_2$ only during cooling from about 900° F. to 700° F. as in Run 13 than with prolonged treatment with hydrogen as in Run 5.

Before Run 14 the catalyst was used in a run at 601° F. and before Run 15 the catalyst was used in a run at 806° F. The data for Runs 14 and 15 show that heating in $H_2$ at 900° F. for about 16 hours gave a quite active catalyst.

All of the runs in Table 4, except Run 13 which used regenerated catalyst that was reduced only during cooling from about 900° F. to 700° F., gave higher conversions than Runs 10–12, Table 3 of Example III. The only known difference is that the hexene-1 feed used in Runs 10–12 was purified to remove dissolved oxygen and other impurities as shown in the footnote (a) of Table 3. The results appear unusual in that feed purification would normally be expected to increase rather than reduce conversion.

The runs shown in Table 4, Runs 5, 13, 14, and 15, are at comparable reaction temperatures of 705°–704°–703°–704° F. As discussed above runs intervening between Run 5 and Run 13 were at 807° F. and 909° F., otherwise using the same feed and conditions. The run at 807° F. showed 9.4% conversion with disproportionation to lower and higher molecular weight products. The run at 909° F., however, began to evidence some cracking, indicating that the LHSV was too low for the higher temperatures. As discussed hereinbefore, generally the LHSV (or GHSV) should be increased as reaction temperatures are increased.

In between Runs 13 and 14, a run was made at a process temperature of 601° F., otherwise with the same feed and conditions. The run at 601° F. showed 8.2% conversion with disproportionation to products of lower and higher molecular weight.

In between Runs 14 and 15, a run was made at a process temperature of 806° F., otherwise with the same feed and conditions. The run at 806° F. showed 10.3% conversion with disproportionation to products of lower and higher molecular weight.

The disclosure, including data, has illustrated the value and effectiveness of our invention. The examples, the knowledge and background of the field of the invention and of general principles of chemistry and other applicable sciences have formed the bases from which the broad description of the invention, including the ranges of the conditions and the generic groups of operant components have been developed, and have formed and bases for our claims here appended.

We claim:

1. A catalyst composition consisting essentially of at least one rare earth metal oxide in an effective amount supported on silica, wherein said rare earth metal oxide is the oxide of yttrium, lanthanum, cerium, praseodymium, dysprosium, or mixture thereof, activated by
   (a) treatment in hydrogen, nitrogen, or mixture at elevated temperatures, or
   (b) by treatment in a molecular oxygen containing gas at elevated temperatures followed by step (a).

2. The catalyst composition according to claim 1 wherein said rare earth metal oxide is yttrium oxide.

3. The catalyst composition according to claim 1 wherein said rare earth metal oxide is lanthanum oxide.

4. The catalyst composition according to claim 1 wherein said rare earth metal oxide is cerium oxide, activated in hydrogen.

5. The catalyst composition according to claim 1 wherein said rare earth metal oxide is praseodymium oxide, activated in nitrogen.

6. The catalyst composition according to claim 1 wherein said rare earth metal oxide is dysprosium oxide.

7. The catalyst composition according to claim 1 wherein said silica-supported rare earth metal oxide contains from about 0.05 to 20 weight percent of the rare earth expressed as the rare earth metal based on the total weight of catalyst including silica support.

8. A catalyst composition consisting essentially of a rare earth metal oxide supported on silica, calcined in a molecular-oxygen-containing atmosphere, followed by activation treatment with hydrogen, nitrogen, or admixture at elevated temperatures, wherein said rare earth metal oxide is selected from the group consisting of the oxides of yttrium, lanthanum, cerium, praseodymium, dysprosium, and mixtures, and wherein said catalyst contains about 0.05 to 20 weight percent of the rare earth oxide expressed as the metal based on the total weight of catalyst including silica support.

9. The catalyst composition according to claim 8 wherein said catalyst contains about 0.5 to 15 weight percent rare earth metal oxide calculated as rare earth metal based on rare earth metal plus silica.

10. The catalyst composition according to claim 8 wherein said rare earth metal oxide is yttrium oxide.

11. The catalyst composition according to claim 8 wherein said rare earth metal oxide is lanthanum oxide.

12. The catalyst composition according to claim 8 wherein said rare earth metal oxide is cerium oxide, activated in hydrogen.

13. The catalyst composition according to claim 8 wherein said rare earth metal oxide is praseodymium oxide activated in nitrogen.

14. The catalyst composition according to claim 8 wherein said rare earth metal oxide is dysprosium oxide.

15. A catalyst composition consisting essentially of a rare earth metal oxide supported on silica containing about 0.05 to 20 weight percent of rare earth metal oxide expressed as the metal based on the total catalyst composition, prepared by the process which comprises the steps of:
- contacting a high specific surface area silica with at least one said rare earth metal oxide, or a solution of a rare earth metal compound wherein said compound is convertible to the oxide on calcination, thereby preparing a composite,
- optionally calcining said composite in a molecular oxygen-containing atmosphere at a temperature in the range of about 600° F. to 1500° F. for a suitable time, and
- activating at elevated temperatures in a hydrogen, nitrogen, or admixture thereof atmosphere for a time sufficient to activate said catalyst.

16. The catalyst composition according to claim 15 wherein said rare earth metal oxide is yttrium oxide on silica.

17. The catalyst composition according to claim 15 wherein said rare earth metal oxide is lanthanum oxide on silica.

18. The catalyst composition according to claim 15 wherein said rare earth metal oxide is cerium oxide on silica activated with hydrogen.

19. The catalyst composition according to claim 15 wherein said rare earth metal oxide is praseodymium oxide activated with nitrogen.

20. The catalyst composition according to claim 15 wherein said rare earth metal oxide is dysprosium oxide on silica.

* * * * *